United States Patent
Liao et al.

(10) Patent No.: US 11,047,012 B2
(45) Date of Patent: Jun. 29, 2021

(54) METHOD FOR DETECTING THE RISK AND PROGNOSIS OF ADULT-ONSET STILL'S DISEASE

(71) Applicant: Taichung Veterans General Hospital, Taichung (TW)

(72) Inventors: Tsai-Ling Liao, Taichung (TW); Der-Yuan Chen, Taichung (TW)

(73) Assignee: TAICHUNG VETERANS GENERAL HOSPITAL, Taichung (TW)

( * ) Notice: Subject to any disclaimer, the term of this patent is extended or adjusted under 35 U.S.C. 154(b) by 0 days.

(21) Appl. No.: 16/014,975

(22) Filed: Jun. 21, 2018

(65) Prior Publication Data
US 2019/0345555 A1 Nov. 14, 2019

(30) Foreign Application Priority Data
May 9, 2018 (TW) .................................. 107115833

(51) Int. Cl.
*C12Q 1/6883* (2018.01)
*G01N 33/68* (2006.01)

(52) U.S. Cl.
CPC ....... *C12Q 1/6883* (2013.01); *G01N 33/6893* (2013.01); *C12Q 2600/106* (2013.01); *C12Q 2600/158* (2013.01); *C12Q 2600/178* (2013.01); *G01N 2333/54* (2013.01)

(58) Field of Classification Search
CPC .. A61K 31/506; A61K 31/519; A61K 38/177; A61K 38/179
See application file for complete search history.

(56) References Cited

U.S. PATENT DOCUMENTS 7,498,321 B2 * 3/2009 Biggadike ............... A61P 29/00
514/172
8,236,820 B2 * 8/2012 Rigas ..................... A61P 25/00
514/320

FOREIGN PATENT DOCUMENTS

WO WO-2015032932 A1 * 3/2015

OTHER PUBLICATIONS

Myo clinic, accessed on Apr. 25, 2019, (Year: 2019).*
Liao et al., Scientific Reports, 7, Jun. 23, 2017. (Year: 2017).*
Kawashima et al. Arthritis & Rheumatism, vol. 44, No. 3, Mar. 2001, pp. 550-560. (Year: 2001).*
NORD, published in 2009, 2012, & 2015 (Year: 2015).*
FDA New Release, Jun. 16, 2020. (Year: 2020).*
Mi-Hyun Ahn et al., Expert Review of Molecular Diagnostics, 19:8. 655-657, 2019 (Year: 2019).*

* cited by examiner

*Primary Examiner* — Jean P Cornet
(74) *Attorney, Agent, or Firm* — Muncy, Geissler, Olds & Lowe, P.C.

(57) ABSTRACT

The present invention discloses a new biomarker miR-134, miR-223, or IL-18, which is positively correlated with AOSD and activities thereof. By detecting the expression level of at least one biomarker in a sample, an effect of detecting the risk and prognosis of a sample provider suffering from a disease is achieved.

3 Claims, 15 Drawing Sheets
Specification includes a Sequence Listing.

```
Gene                           Genebank Accession No.   Alignment of fragments Human IL-18BP 3'UTR            AF110801                 1891 5'UGCCUGAAAGAGACACAGUCACA3'1913
                                                                        :||  |||||||
hsa miR-134                                                  3'GGGGAGACCAGUUG-GUCAGUGU5'
                                                                        :||  |  |  |  |
Human IL-18BP 3'UTR mutant                                   5'UGCCUGAAAGAGACACUGACUCA3'
```

METHOD FOR DETECTING THE RISK AND PROGNOSIS OF ADULT-ONSET STILL'S DISEASE

BACKGROUND OF THE INVENTION

1. Field of the Invention

The present invention relates to a biomarker and a use thereof in detection, and in particular to a method for detecting the risk and prognosis of adult-onset Still's disease.

2. Description of the Related Art

Adult-onset Still's disease (AOSD) is an immune disease that invades multiple organs and has the clinical features of persistent high spiking fevers, evanescent rash, arthritis, sore throat, enlarged lymph nodes, hepatosplenomegaly, leukocytosis with predominant neutrophils, or that invades other internal organs.

However, because the clinical features of AOSD are not distinctive, when the patients are attacked by the disease, they are often given unwanted antibiotics because of persistent fever, or receive unnecessary invasive tests that, however, fail to detect the cause of disease. At present, the diagnosis of AOSD mainly depends on the doctor's comprehensive judgment of the clinical symptoms, the laboratory test data, and the status at treatment. As a result, most patients cannot be diagnosed quickly and accurately, resulting in delayed treatment of the disease.

It can be seen from the above that there is currently a need in clinic for a tool and a method that can be used to diagnose AOSD.

SUMMARY OF THE INVENTION

The main object of the present invention is to provide a microRNA that can be used to detect the occurrence, prognosis and AOSD activity. In particular, by determining the expression levels of miR-134 or IL-18 in a sample, it is possible to evaluate the disease activity in a patient with AOSD, evaluate the prognosis of the patient with AOSD, or determine the risk of the sample provider suffering from AOSD.

Another object of the present invention is to provide a pharmaceutical composition designed to target miR-134 or miR-223, to achieve the effect of improving or slowing down AOSD.

To achieve the above objects, in an embodiment of the present invention, a method for treating AOSD, which comprises administering a pharmaceutical composition to an individual suffering from AOSD to improve or reduce AOSD and symptoms thereof. The pharmaceutical composition comprises an effective amount of a miR-134 inhibitor, a miR-223 inhibitor or a TLR3 receptor inhibitor.

Furthermore, the pharmaceutical composition is capable of reducing the expression of IL-18 in the individual.

In another embodiment of the present invention, a method for detecting the therapeutic effectiveness for AOSD, which comprises:
detecting the expression of a biomarker in a sample to obtain a first expression level, where the biomarker is selected from the group consisting of miR-134, miR-223 and IL-18;
administering a treatment to the sample;
after the treatment is received, detecting the expression of the biomarker in the sample, to obtain a second expression level; and
comparing the first expression level with the second expression level, where when the second expression level is higher than the first expression level, the treatment is shown to be ineffective in the treatment of AOSD; and when the second expression level is lower than the first expression level, the treatment is shown to be effective in the treatment of AOSD.

In an embodiment of the present invention, the sample is preferably blood.

The method for detecting the expression of miR-134, miR-223, or IL-18 in a sample is a technique well-known in the art, such as QRT-PCR, ELISA, and so on.

Further, in another embodiment of the present invention, a pharmaceutical composition for treating AOSD, which comprises an effective amount of a miR-134 inhibitor, a miR-223 inhibitor, and/or a TLR3 receptor inhibitor, and at least a pharmaceutically acceptable carrier.

BRIEF DESCRIPTION OF THE DRAWINGS

FIG. 6 shows the alignment of a sequence of IL-18BP that is reverse complementary to miR-134, and miR-134.

DETAILED DESCRIPTION OF THE PREFERRED EMBODIMENTS

Figure 1A:
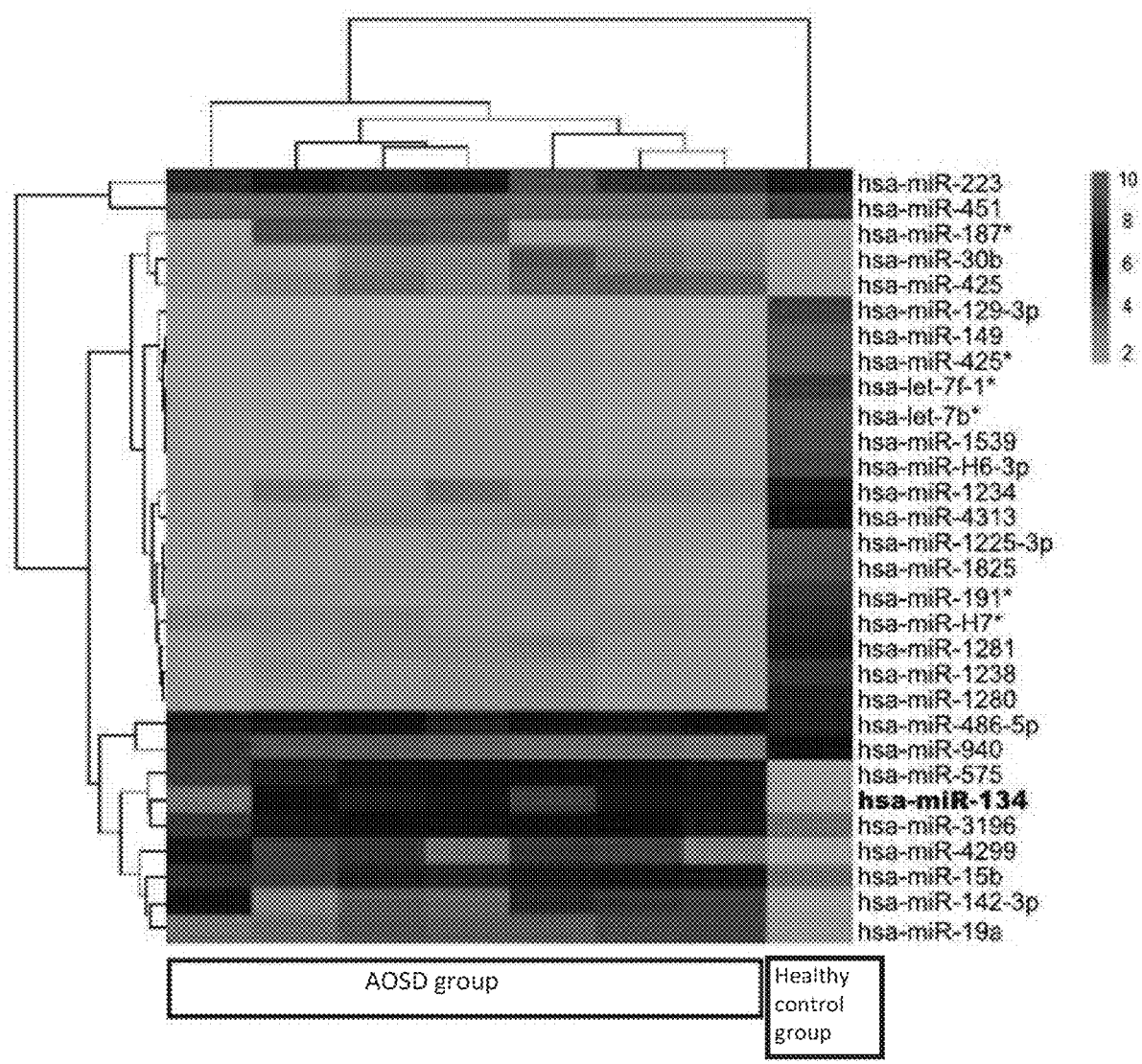
FIG. 1A shows the differential expressions of miRNAs in the plasma of the AOSD group and the healthy control group as assayed by using a miRNA microarray, in which the relative expression levels of the miRNAs are indicated in different colors, wherein red indicates that the relative expression level is higher than the median of all samples, and green indicates that the relative expression level is lower than the median of all samples.

The present invention discloses use of at least one microRNA and/or a protein as a biomarker in AOSD to detect the disease AOSD activity, the risk of developing AOSD and the prognosis of AOSD, in which the microRNA is miR-134 or miR-223, and the protein is IL-18.

Further, the expression levels of miR-134, miR-223, and IL-18 are positively correlated with the disease activity, and arthritis and other signs of AOSD. Therefore, by detecting the expressions of miR-134, miR-223, and IL-18 in a sample such as blood, the risk of the sample provider suffering from AOSD, or the prognosis of the patient with AOSD after receiving an intended treatment, or the disease activity in the patient with AOSD can be evaluated.

The disease activity score, disease activity or activity score mentioned in the present invention refers to the activity level of a disease judged clinically by a physician. With respect to the AOSD discussed in the present invention, if a patient is determined by a physician to have a high disease activity index, it is called the active AOSD, and if a patient is determined by a physician to have a low disease activity index, it is called the inactive AOSD.

To further confirm the efficacy of the present invention, the present invention will be described below by way of examples in connection with the drawings.

The following clinical trials were approved by the Clinical Trial Ethics Committee of Taichung Veterans General Hospital (CF11224) and the written consents of all subjects are got in accordance with the relevant regulations.

The samples described in the following examples, if not otherwise stated, are plasma samples provided by subjects in each group.

Example 1: Clinical Trial

Test group: A total of 12 consecutive patients with AOSD (hereinafter referred to as patients with AOSD) who met the Yamaguchi criteria and did not receive treatment. None of these patients with AOSD had any infection, malignancies, or other rheumatic diseases. The disease activity in each of the patients with AOSD was calculated using the modified Pouchot's score.

The common manifestations in these patients with AOSD included spiking fever in 9 patients (75.0%), evanescent rash in 8 patients (66.7%), sore throat in 7 patients (58.3%), arthritis in 5 patients (41.7%), enlarged lymph nodes in 4 patients (33.3%), and hepatosplenomegaly in 3 patients (25.0%).

Healthy control group: Healthy adults of suitable age having no rheumatic diseases were enrolled.

Verification group: 18 patients with AOSD were enrolled for immediate validation by QRT-PCR of the differential expressions of miRNAs from a microarray assay.

Disease control group: 22 patients with systemic lupus erythematosus who met the criteria set by the American College of Rheumatology were enrolled. These patients had partially the same clinical manifestations as those with AOSD.

There were no significant differences in the age of the patients and the proportion of women between the test group and the healthy control group.

The patients with AOSD in all the groups received corticosteroids and/or non-steroidal anti-inflammatory drugs (NSAIDs) after miRNA detection. Among them, 10 patients with AOSD were treated with methotrexate, 8 patients with AOSD were treated with hydroxychloroquine, and 5 patients with AOSD were treated with sulfasalazine. In the follow-up period of two years, 3 patients received the treatment with an IL-6 receptor inhibitor (tocilizumab).

Example 2: Microarray Analysis

The test group, the healthy control group, and the disease control group were assayed by using a miRNA microarray (Agilent Technologies, Palo Alto, Calif., USA) The miRNA microarray had 887 miRNAs.

The analytical procedure was as follows. Total RNA was obtained from a sample by extraction with the TRIzol reagent (Invitrogen, Thermo Fisher Scientific, USA) and purification with the RNeasyMinElute Cleanup kit (QIAGEN, Germany) to obtain total RNA from the sample.

100 ng of total RNA was dehydrated, and labeled with pCp-Cy3 by using the Agilent miRNA Complete Labeling and Hyb kits (Agilent Technologies, USA). 2× hybridization buffer (Agilent Technologies, USA) was added to the labeled mixture to a final volume of 45 µl. The scanned images were analyzed by software (Feature Extraction software version 10.7.3.3.1, Agilent Technologies, USA) and the data was analyzed by GeneSpring 7.3.1 (Agilent Technologies, USA).

The signal intensity at each point was obtained by subtracting the local background from the total intensity. The value for each miRNA was generated from the median of every four points. Per-chip normalization was performed, in which the 75th percentile method was used to normalize each chip to a median of the measurements for that chip, and the wafers were compared. Moreover, in order to highlight the characteristics of the miRNAs in each group, per-gene normalization was performed to normalize each gene to a median of the measurements for that gene.

The patents with AOSD in the test group and the subjects in the healthy control group were analyzed by microarray assay. The results are shown in Table 1 below and in FIG. 1A, in which when the value of fold changes in Table 1 is greater than 3.00 or less than 0.330, the difference between the test group and the healthy control group is considered to be significant. The fold change means a result of the test group compared to the healthy control group.

TABLE 1

Differential expressions, assayed by using a miRNA microarray, of miRNAs in the plasma of the test group compared to the healthy control group

| Up-regulated miRNAs | Fold change (median) | Down-regulated miRNAs | Fold change (median) |
| --- | --- | --- | --- |
| hsa-miR-575 | 18.099 | hsa-miR-940 | 0.169 |
| hsa-miR-4299 | 14.766 | hsa-miR-4313 | 0.177 |
| hsa-miR-15b | 11.140 | hsa-miR-1280 | 0.189 |
| hsa-miR-223 | 10.089 | hsa-miR-1281 | 0.206 |
| hsa-miR-142-3p | 5.860 | hsa-miR-486-5p | 0.220 |
| hsa-miR-451 | 5.501 | Hsa-let-7f-1 | 0.228 |
| hsa-miR-134 | 4.660 | hsa-miR-191 | 0.232 |
| hsa-miR-187 | 4.323 | hsa-miR-1234 | 0.243 |
| hsa-miR-19a | 3.509 | hsa-miR-1825 | 0.267 |
| hsa-miR-30b | 3.507 | hsa-miR-129-3p | 0.269 |
| hsa-miR-3196 | 3.491 | hsa-miR-1238 | 0.276 |
| hsa-miR-425 | 3.322 | hsa-miR-1539 | 0.281 |
| | | hsa-miR-149 | 0.287 |
| | | hsa-miR-425 | 0.294 |
| | | hsa-miR-1225-3p | 0.295 |
| | | hsa-miR-21 | 0.313 |

As can be seen from the results of Table 1 and FIG. 1A, 28 miRNAs in the plasma of patients with AOSD have significant expression. Among them, 12 miRNAs are up-regulated and 16 miRNAs are down-regulated compared to the healthy control groups.

Example 3: Quantitative Reverse Transcription Polymerase Chain Reaction (QRT-PCR)

The miRNA expressions in a sample were detected using the TaqMan MicroRNA detection kit (Applied Biosystems, Thermo Fisher Scientific, USA) and QRT-PCR was performed in the StepOne Plus real-time PCR system. Small nuclear RNA (hereinafter referred to as RUN6) and synthetic cel-miR-39 (hereinafter referred to as cel-miR-39 cel-miR-39) were respectively used as an internal control gene in cells and plasma. The multiple expression of the target gene was obtained by calculating the average expression of the target gene relative to the internal control gene in the sample by comparative threshold cycle (Ct) method, and evaluated by $2^{-\Delta\Delta Ct}$, where $\Delta\Delta Ct$ is the $(Ct_{miRNAsgene} - Ct_{Rnu6/cel-miR-39})$ of the patient from which the average $(Ct_{miRNAs\ gene} - Ct_{Rnu6/cel-miR-39})$ of the internal control gene is subtracted.

To detect miRNAs, the total RNA was reverse transcribed into the target mRNA using oligo(dT)20 as a primer (SuperScript First-Strand Synthesis System, Invitrogen, Thermo Fisher Scientific, USA). The single-stranded cDNA was obtained by QRT-PCR using the TaqMan gene expression detection kit (Applied Biosystems, Thermo Fisher Scientific, USA). The GAPDH gene was used as an internal control gene.

Example 4: Cell Culture

Peripheral blood mononuclear cells, human monocyte cell line U937 (ATCC CRL1593, hereinafter referred to as U937 cell) and THP-1 cells (ATCC TIB-202) isolated from the subject were respectively cultured in RPMI medium 1640 (Gibco, Thermo Fisher Scientific, USA) supplemented with 10% fetal bovine serum, 1× non-essential amino acids, 100 unit/ml penicillin and 100 unit/ml streptomycin in 5% carbon dioxide at 37° C.

To induce the cells to differentiate macrophages, the U937 cells and THP-1 cells (1×10 6 cells/mL) were cultured on a medium and treated with 10 ng/ml PMA (phorbol myristate acetate) overnight.

Example 5: Verification of the Results from Microarray Assay

Figure 1B:
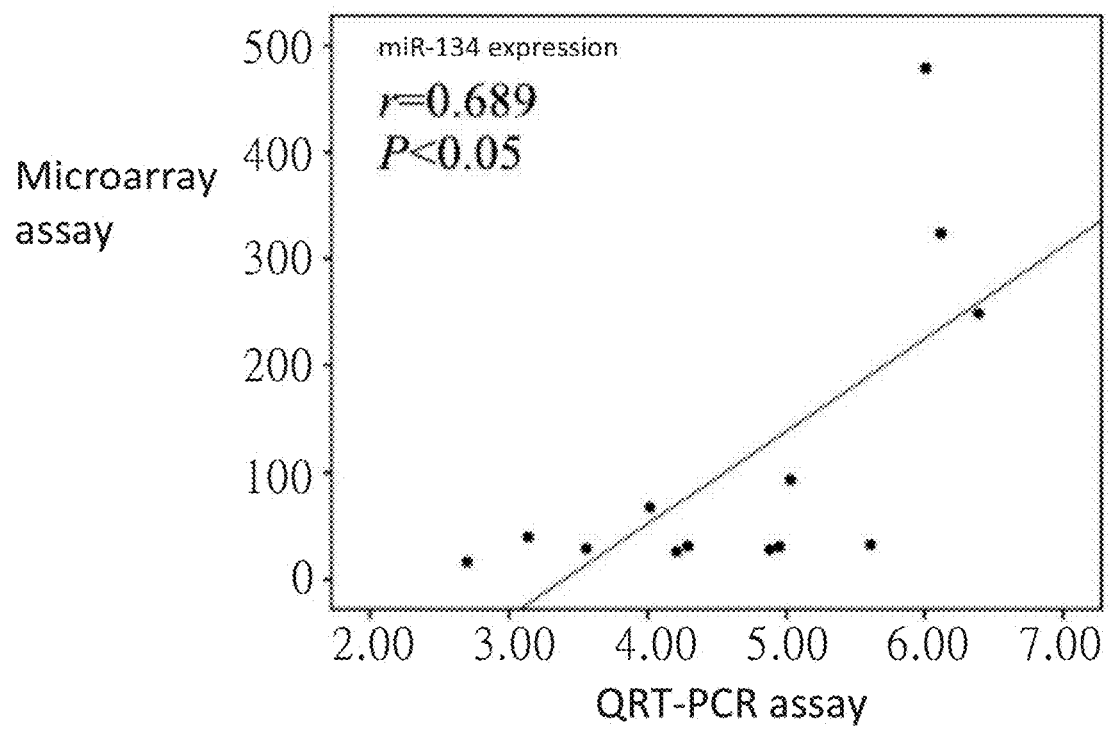
FIG. 1B shows the verification by QRT-PCR of the differential expression of miR-134 in the plasma of patients with AOSD as assayed by using a miRNA microarray.

The miRNA expressions in the plasma samples from each subject in the healthy control group and the test group were analyzed by QRT-PCR. The results from QRT-PCR analysis are compared with those obtained by microarray assay in Example 2, showing that the results from QRT-PCR analysis are consistent with those obtained by microarray assay. For example, referring to FIG. 1B, the expressions of miR-134 analyzed by QRT-PCR and microarray assay are compared, and found to be consistent.

Example 6: miR-134 and miR-223 are Biomarkers in AOSD

The miR-134 and miR-223 expressions in the plasma and in peripheral blood mononuclear cells of patients with different AOSD activities and subjects in the disease control group and the healthy control group were analyzed by QRT-PCR. The results are shown in FIG. 2A to FIG. 2D. The peripheral blood mononuclear cells were isolated from venous blood using the icoll-Paque™ PLUS kit (GE Healthcare Biosciences AB, Uppsala, Sweden).

Figure 2A:
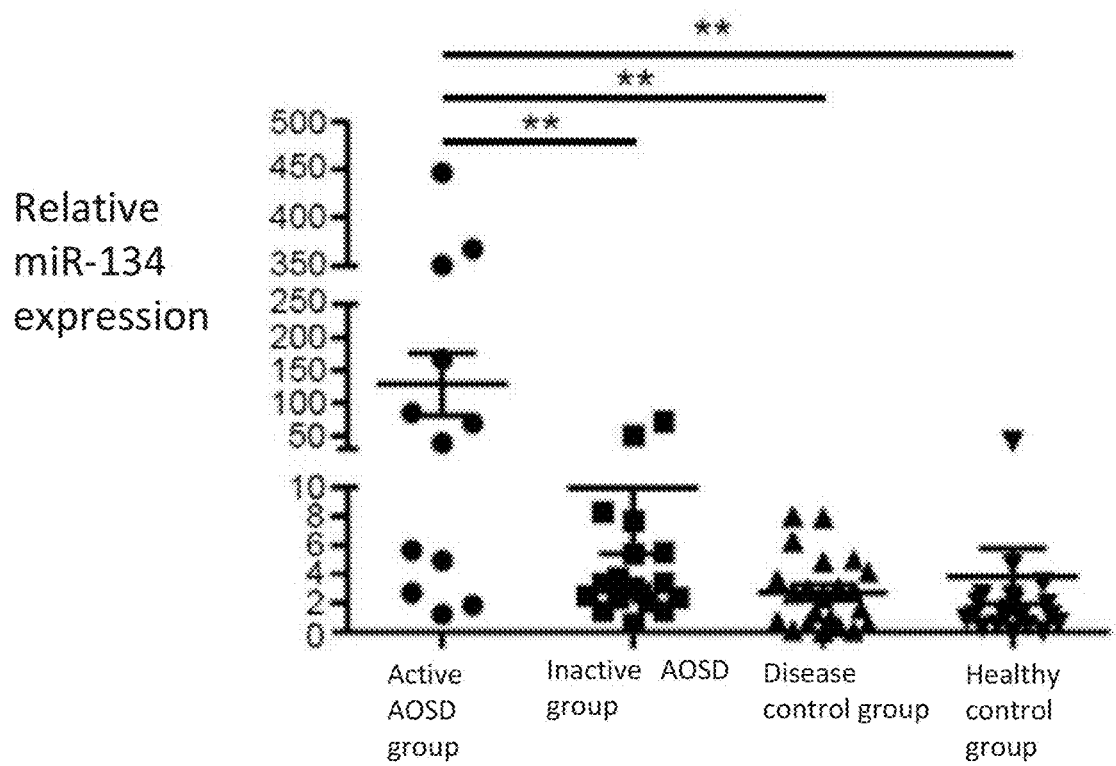
FIG. 2A shows the miR-134 expressions, as detected by QRT-PCR, in the plasma of patents with different AOSD activity score, and subjects in a disease control group and a healthy control group.

Referring to FIG. 2A, the miR-134 expression level determined is 128.60±47.72 folds in the plasma of patients with active AOSD, 10.00±4.55 folds in the plasma of patients with inactive AOSD, 2.86±0.53 folds in the plasma of subjects in the disease control group, and 5.25±2.26 folds in the plasma of subjects in the healthy control group. The results in FIG. 2B show that the miR-134 expression level determined is 147.70±28.25 folds in the peripheral blood mononuclear cells of patients with active AOSD, 1.91±0.44 folds in the peripheral blood mononuclear cells of patients with inactive AOSD, 0.16±0.04 fold in the peripheral blood mononuclear cells of subjects in the disease control group, and 0.53±0.13 fold in the peripheral blood mononuclear cells of subjects in the healthy control group.

Figure 2B:
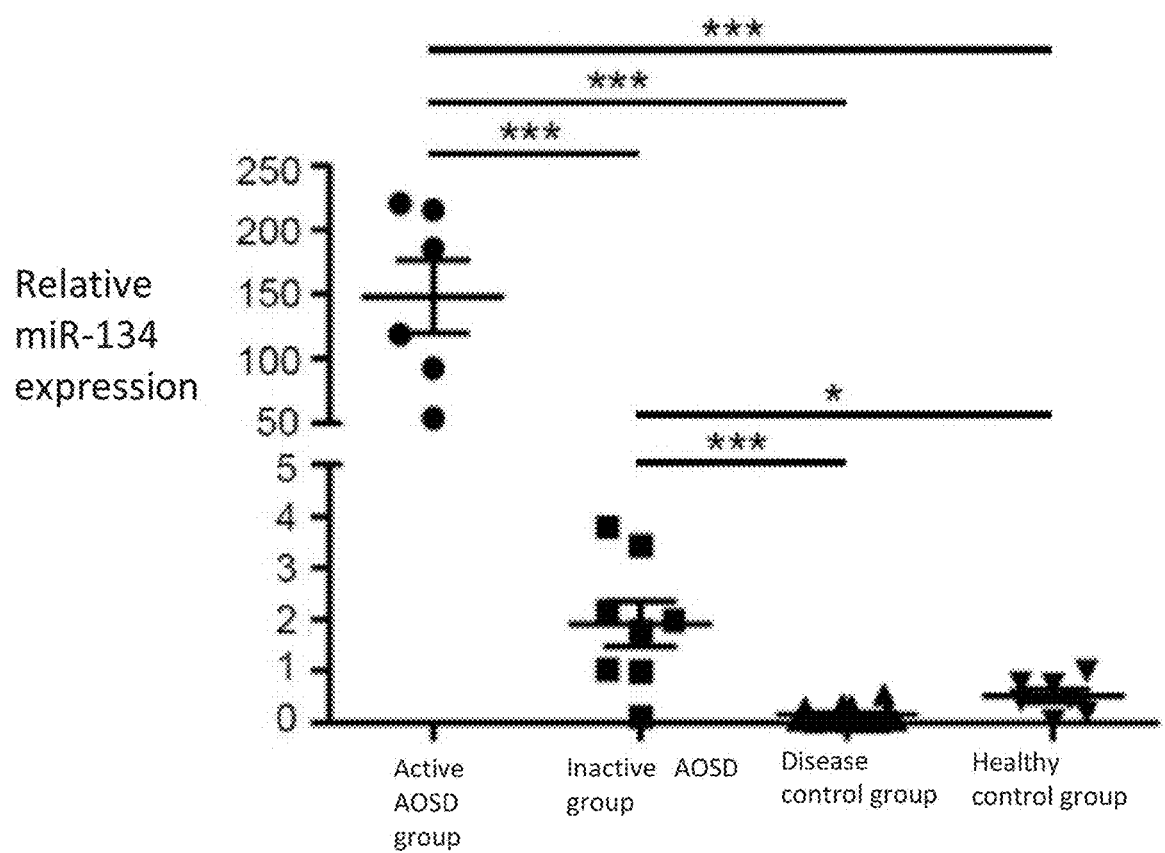
FIG. 2B shows the miR-134 expressions, as detected by QRT-PCR, in peripheral blood mononuclear cells derived from patents with different AOSD activity score, and subjects in a disease control group and a healthy control group.
Figure 2C:
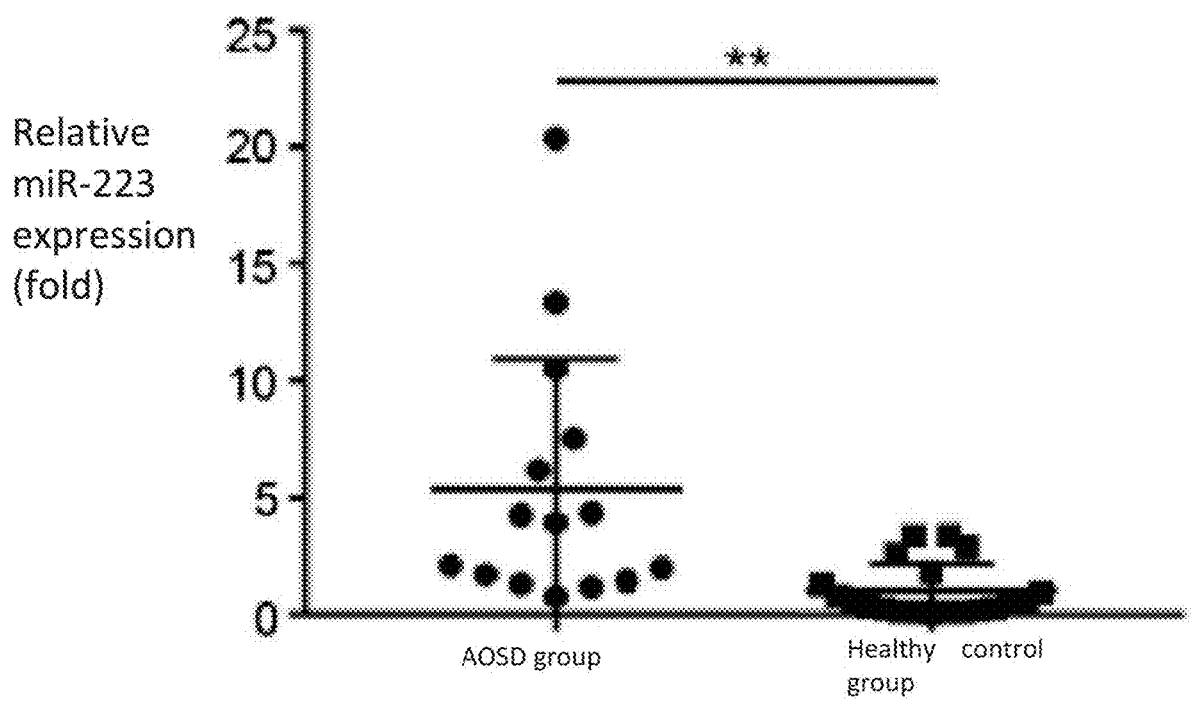
FIG. 2C shows the miR-223 expressions, as detected by QRT-PCR, in the plasma of patients with AOSD and subjects in a healthy control group.
Figure 2D:
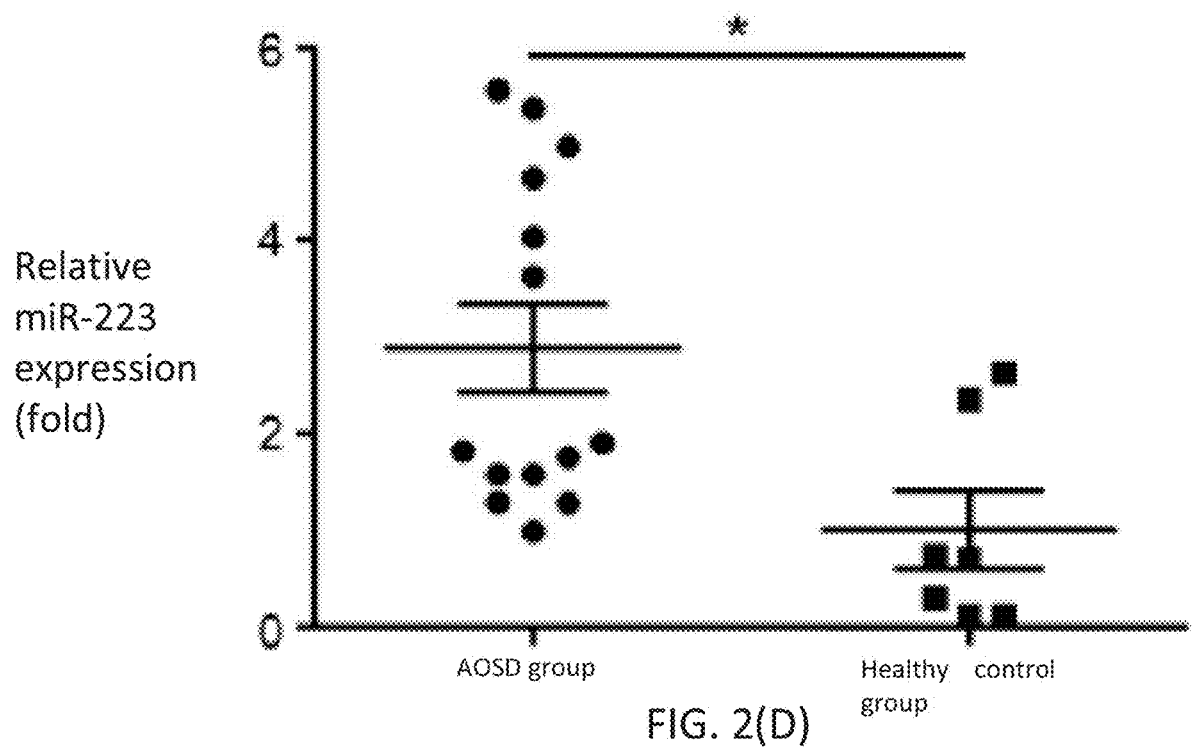
FIG. 2D shows the miR-223 expressions, as detected by QRT-PCR, in peripheral blood mononuclear cells derived from patents with AOSD and subjects in a healthy control group, wherein the expression level in the patients with AOSD is 2.88±0.46 folds, and the expression level in the healthy control group is 1.00±0.15 fold.

Referring to FIG. 2C, the miR-223 expression level determined is 5.41±1.44 folds in the plasma of patients with active AOSD, and 1.00±2.58 folds in the plasma of subjects in the healthy control group. The results in FIG. 2D show that the miR-223 expression level determined is 2.88±0.46 folds in the peripheral blood mononuclear cells of patients with active AOSD, and 1.00±0.15 folds in the peripheral blood mononuclear cells of subjects in the healthy control group.

It can be known from the results in FIGS. 2A and 2B that the miR-134 expressions in the plasma and peripheral blood mononuclear cells of patients with AOSD are significantly higher than those in the plasma and peripheral blood mononuclear cells of patients with systemic lupus erythematosus and healthy subjects. Moreover, it can be known from the analysis results in peripheral blood mononuclear cells that the miR-134 expression is positively correlated with the AOSD activity. Based on this, miR-134 is useful as a biological marker in the identification of AOSD.

Similarly, the miR-223 expressions in the plasma and peripheral blood mononuclear cells of patients with AOSD and subjects in the healthy control group were analyzed by QRT-PCR. The results are shown in FIG. 2C and FIG. 2D, indicating that whether the miR-223 is derived from the plasma or from the peripheral blood mononuclear cells, the expression level in patients with AOSD is significantly higher than that in the subjects in the healthy control group. That is, the miR-223 expression level is definitely positively correlated with the AOSD activity. miR-223 is useful as a biomarker in the indemnification of AOSD.

Figure 3A:
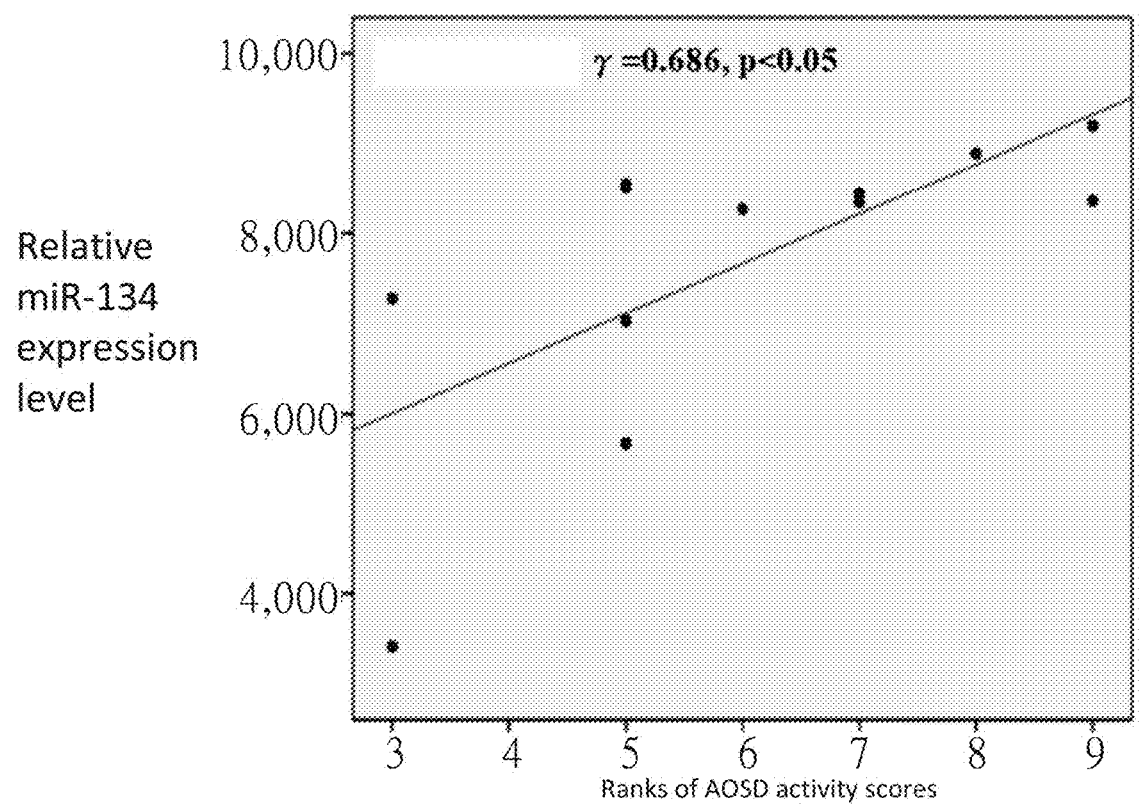
FIG. 3A shows the verification by QRT-PCR of the correlation between the miR-134 expression levels and the AOSD activity scores.
Figure 3B:
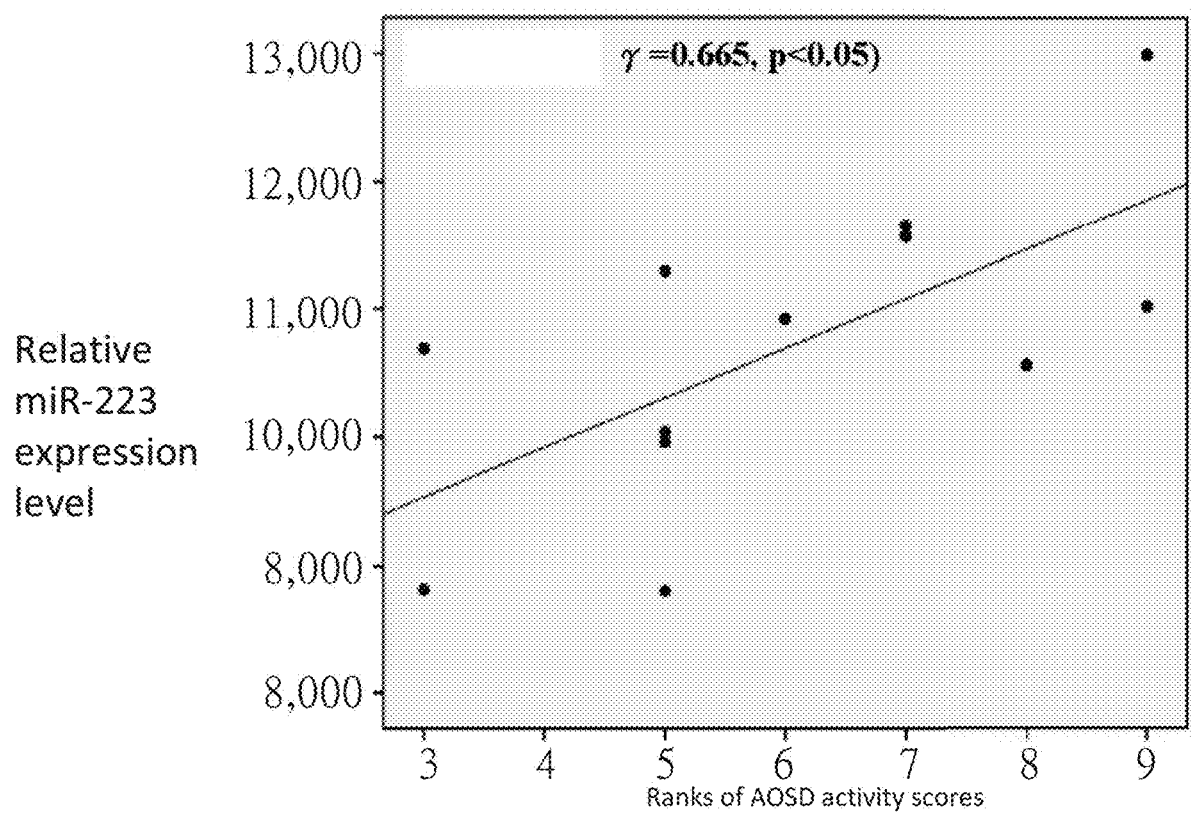
FIG. 3B shows the verification by QRT-PCR of the correlation between the miR-223 expression levels and the AOSD activity scores.
Figure 4:
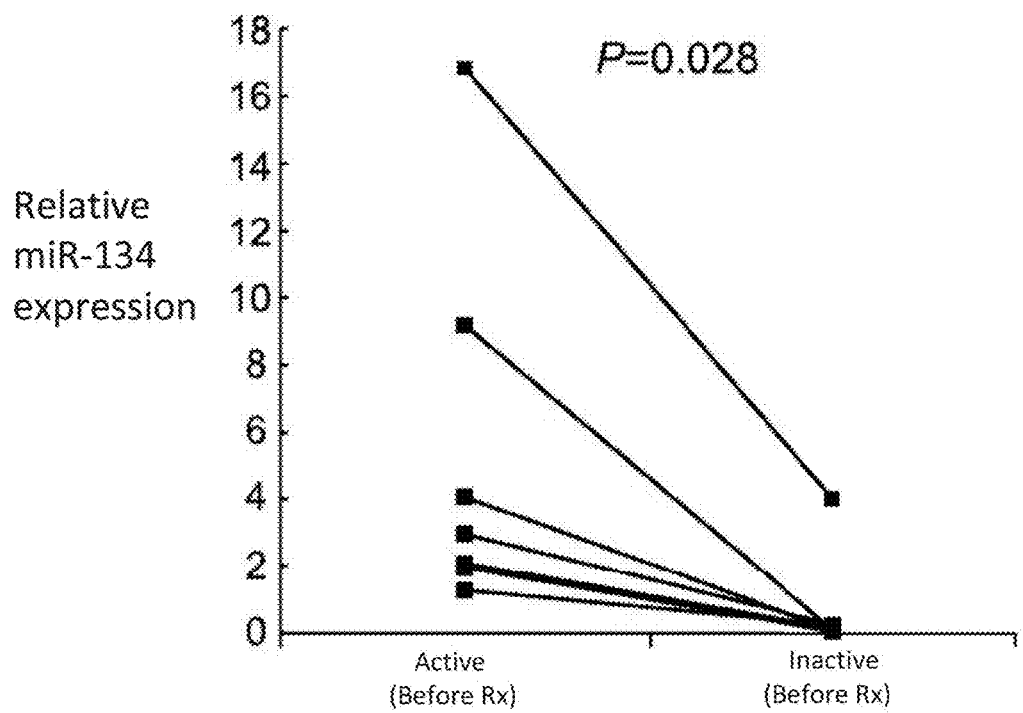
FIG. 4 shows that the miR-134 expression declines significantly 6 months after the patients with AOSD receive treatment, and is parallel to clinical remission of the patient with AOSD.

Example 7: The miR-134 and miR-223 Expressions are Positively Correlated with the AOSD Activity Referring to FIG. 3, it can be known from the results of QRT-PCR analysis that the expression levels of miR-134 and miR-223 are definitely positively correlated with the AOSD activity among the miRNAs with differential expressions. Referring to FIG. 4, 6 months after the patients with AOSD receive the treatment, the expression of miR-134 declines significantly (mean±SEM, 5.30±2.19 vs. 0.84±0.56, P<0.05), and is parallel to clinical remission (activity index 5.7±0.5 vs. 2.0±0.4, P<0.05).

It can be seen that miR-134 and miR-223 are useful as biomarkers in the detection or evaluation of the disease activity in patients with AOSD.

Example 8: The TLR3 Receptor Inhibitor can Modify or Reduce the AOSD Activity

Peripheral blood mononuclear cells (5×105 cells) derived from the subjects were stimulated with different TLR ligands. Finally, the intracellular expression level of miR-134 was measured with the TaqMan MicroRNA test kit. The results are shown in FIG. 5.

Figure 5A:
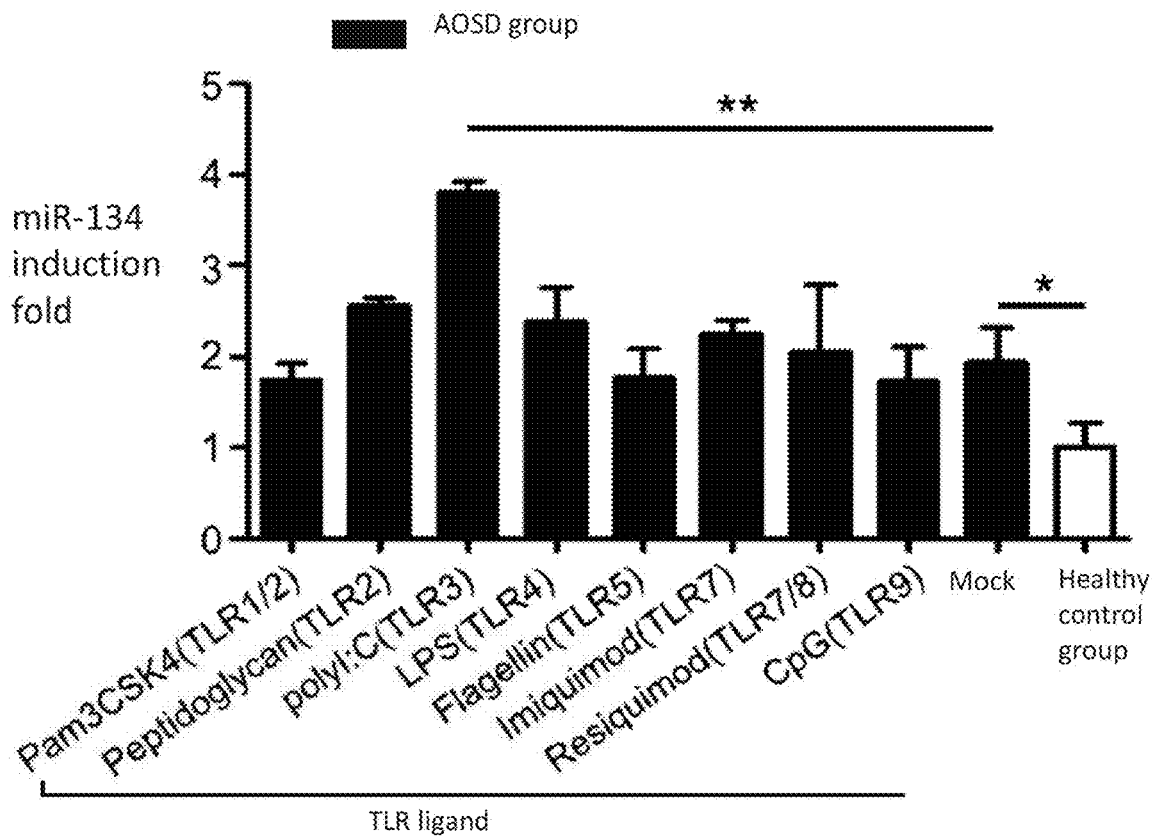
FIG. 5A shows an obvious increase in the intracellular miR-134 expression in TLR ligand-stimulated peripheral blood mononuclear cells derived from patients having AOSD.

From the results in FIG. 5A, it can be seen that the peripheral blood mononuclear cells derived from the patients with AOSD are treated with the TLR3 ligand poly(I:C) (polyriboinosinic:polyribocytidylic acid, 50 μg/ml), the miR-134 expression level in the cells is increased significantly (3.81±0.09 folds).

Figure 5B:
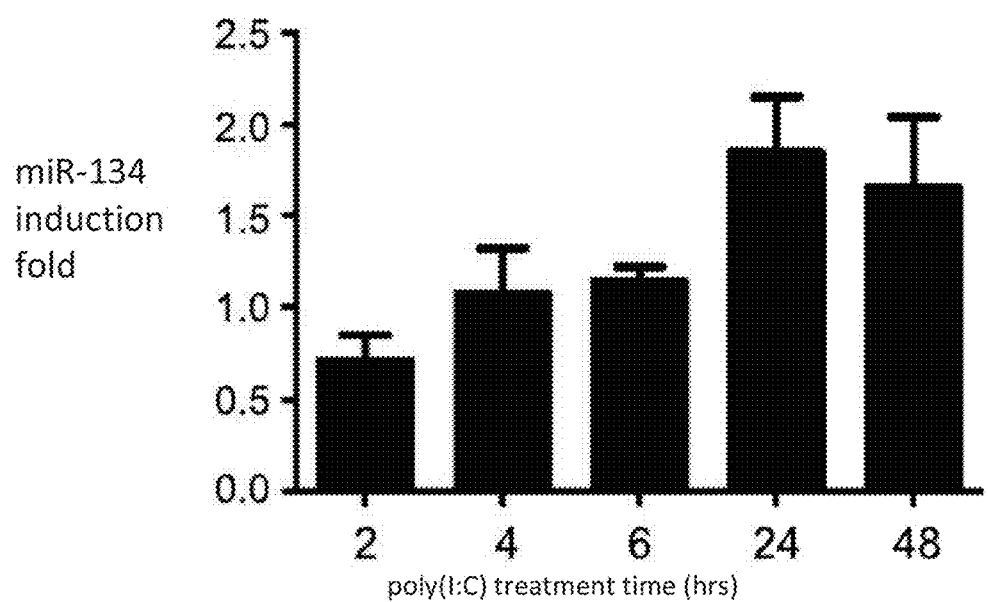
FIG. 5B shows that the intracelluar expression of miR-134 is increased significantly after the THP-1 is stimulated with poly (I:C), and reaches the highest value at 24 hrs.

Further, the THP-1 cells were treated with the TLR3 ligand poly (I:C). The results in FIG. 5B show that the expression of miR-134 in THP-1 cells is also increased significantly, and the expression of miR-134 reaches the highest value (1.92±0.11 folds) at 24 hours after stimulation with poly (I:C).

From the results obtained in this example, it can be seen that stimulation with TLR ligands does induce an increase in the expression level of miR-134, meaning that administration of a TLR3 receptor inhibitor can achieve the treatment of AOSD or the attenuation of the AOSD activity.

Example 9: Production of IL-18BP and Mutants Thereof

Wild human IL-18BP 3'UTR-luciferase reporter plasmid was obtained by amplifying the human IL-18BP mRNA 3'UTR (AF110801.1) and cloning it into the pMIR-REPORT vector carrying luciferase (Ambion, Thermo Fisher Scientific, USA). A mutant human IL-18BP 3'UTR-luciferase reporter plasmid was obtained by mutating the AGTCAC at a give binding site to TGACTC, as shown in FIG. 6.

Example 10: miR-134 Promotes the Over-Expression of Proinflammatory Cytokine IL-18

A miR-134 mimic and a control mimic (Thermo Fisher Scientific, USA) (50 nM) were transferred to U937 cells respectively by using the Neon® transfection system (Invitrogen, Thermo Fisher Scientific, USA), to obtain a miR-134 mimic group and a control mimic group. Non-transfected U937 cells were used as a mock group. Then, the differently treated cells were cultured overnight at 37° C., and then the expression of IL-1β (RayBiotech Inc., Norcross, Ga., USA, IL-6 (PeproTech Inc., Rocky Hill, N.J., USA), IL-17A (RayBiotech Inc., Norcross, Ga., USA), IL-18 (Medical & Biology Laboratories Co, Ltd., Naka-ku, Nagoya, Japan) and TNF-α(R&D Systems, USA) in the culture supernatants of the differently treated cells were detected by ELISA. The results are shown in FIG. 7.

Figure 7A:
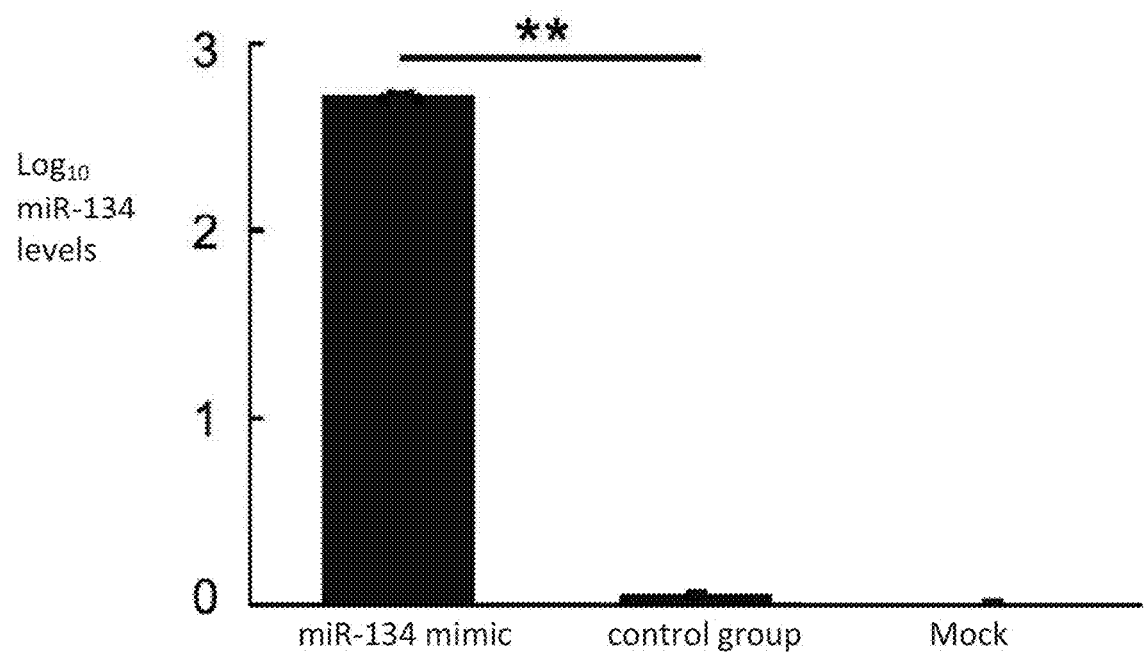
FIG. 7A shows the miR-134 expressions detected in cells in a miR-134 mimic group, a mimic control group, and a mock group.
Figure 7B:
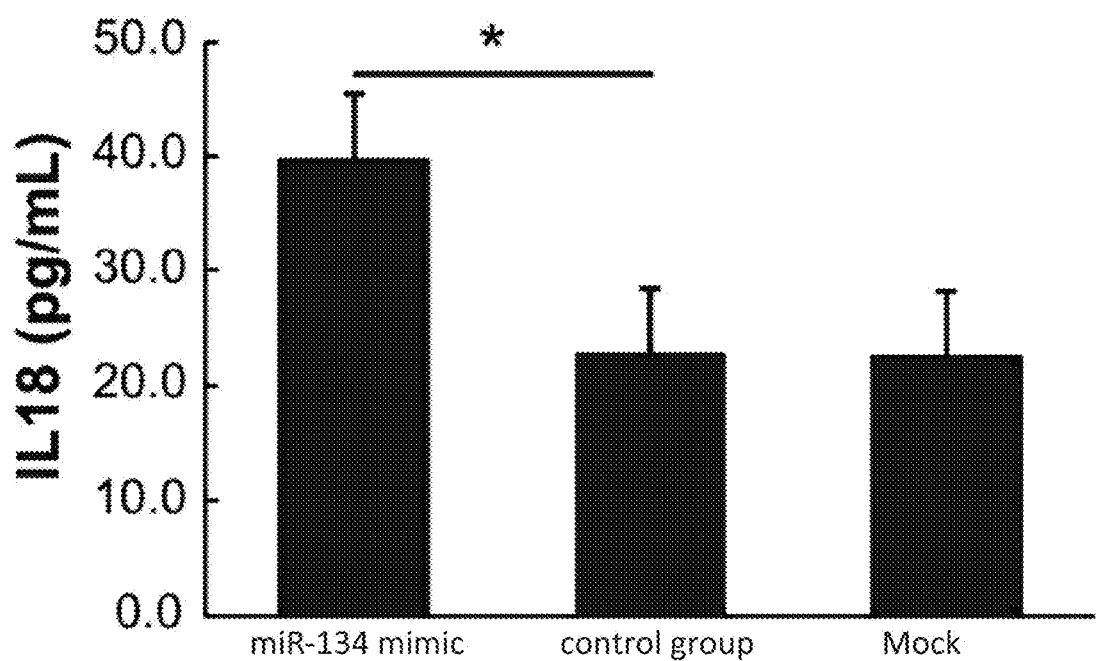
FIG. 7B shows the IL-18 expressions detected in cells in the miR-134 mimic group, the mimic control group, and the mock group.
Figure 7C:
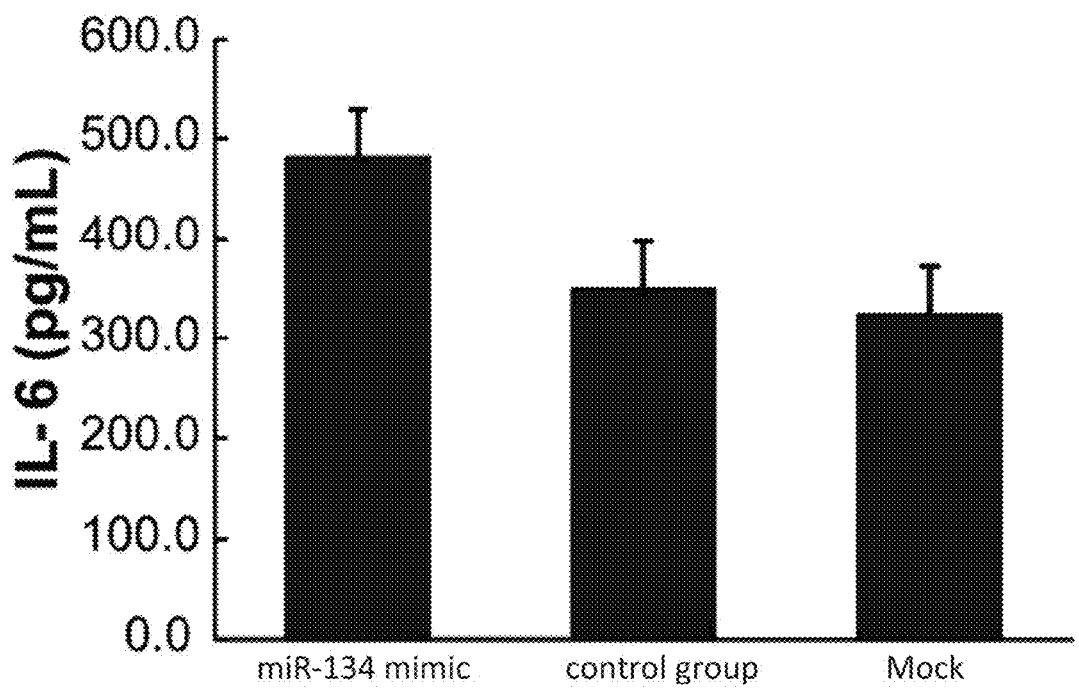
FIG. 7C shows the IL-6 expressions detected in cells in the miR-134 mimic group, the mimic control group, and the mock group.
Figure 7D:
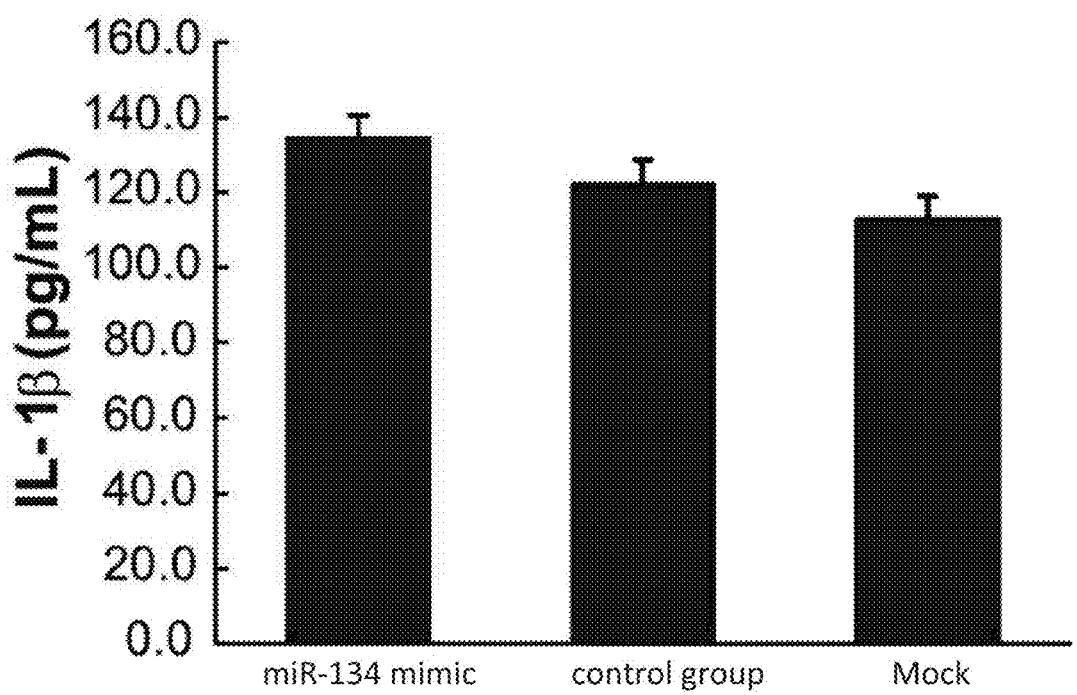
FIG. 7D shows the IL-11 expressions detected in cells in the miR-134 mimic group, the mimic control group, and the mock group.
Figure 7E:
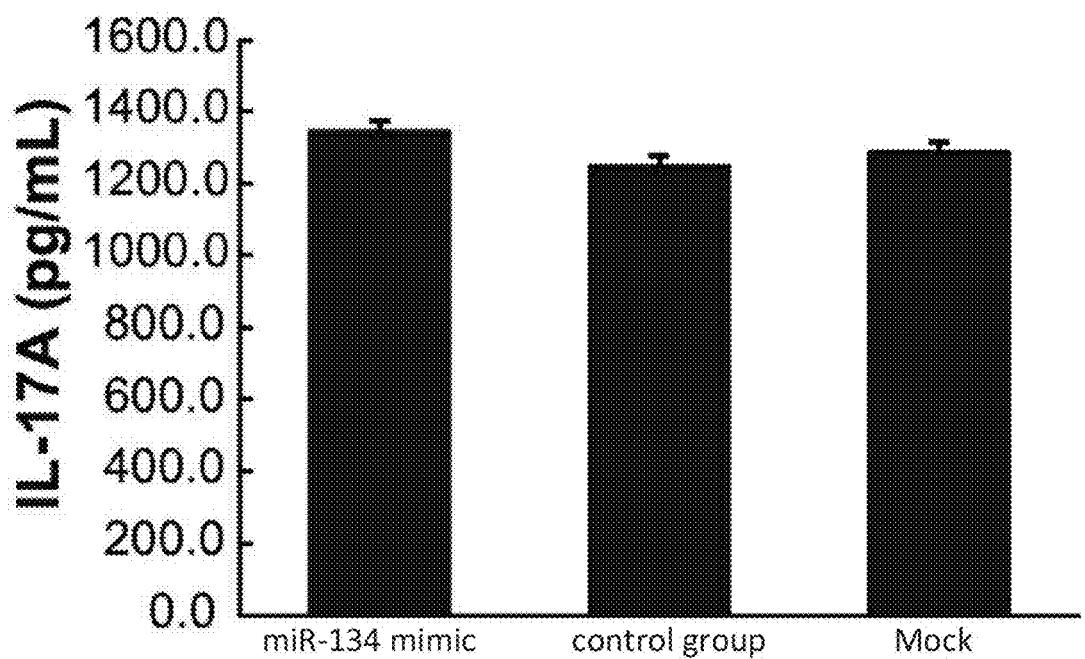
FIG. 7E shows the IL-17A expressions detected in cells in the miR-134 mimic group, the mimic control group, and the mock group.
Figure 7F:
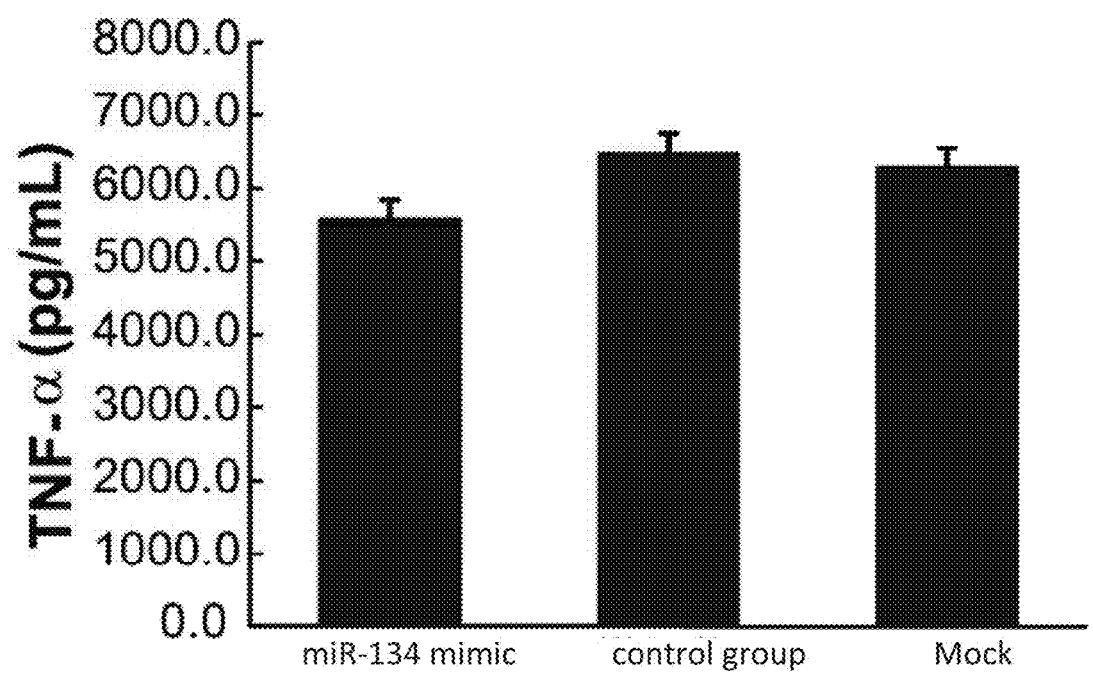
FIG. 7F shows the TNF-α expressions detected in cells in the miR-134 mimic group, the mimic control group, and the mock group.

As can be seen from the results in FIG. 7A, the miR-134 mimic is indeed transfected into the U937 cells. Furthermore, the results in FIG. 7B show that IL-18 is over expressed in the cells of the miR-134 mimic group, with an average expression level of 39.7 pg/ml, which is obviously higher that in the cells of the control mimic group (with an average expression level of 22.7 pg/ml) and in the cells of the mock group (with an average expression level of 22.5 pg/ml). It can be known from the results in FIG. 7C to FIG. 7F that there is no significant difference in the expressions of other proinflammatory cytokines IL-6, IL-1β, IL-17A and TNF-α between the miR-134 mimic group and the control mimic group and mock group. Therefore, it can be seen from the results in FIG. 7 that the overexpression of miR-134 does specifically cause the excessive secretion of IL-18.

This result shows that when overexpressed by miR-134 in a sample, the sample provider is at high risk of innate immune diseases such as AOSD, and the patient has symptoms such as arthritis. If a miR-134 inhibitor is administered to patient, the expression of the proinflammatory cytokine IL-18 in the cells can be effectively inhibited or reduced, thereby achieving the efficacy of slowing down or improving inflammation and related symptoms in patients with AOSD.

Example 11: IL-18BP is a Target of miR-134

293T cells and THP-1 cells were respectively co-transfected with 80 ng of luciferase reporter plasmid, 40 ng of thymidine kinase promoter-*Renilla* luciferase reporter plasmid, and a miR-134 mimic (30 nM), a control mimic (30 nM), a miR-134 inhibitor (50 nM), or a control inhibitor (50 nM), and used as a miR-134 mimic group, a control mimic group, a miR-134 inhibitor group, and a control inhibitor group. The luciferase reporter plasmid was an empty pMIR-REPORT vector, a wild human IL-18BP 3' UTR-luciferase reporter plasmid or a mutant human IL-18BP 3' UTR-luciferase reporter plasmid.

Figure 8:
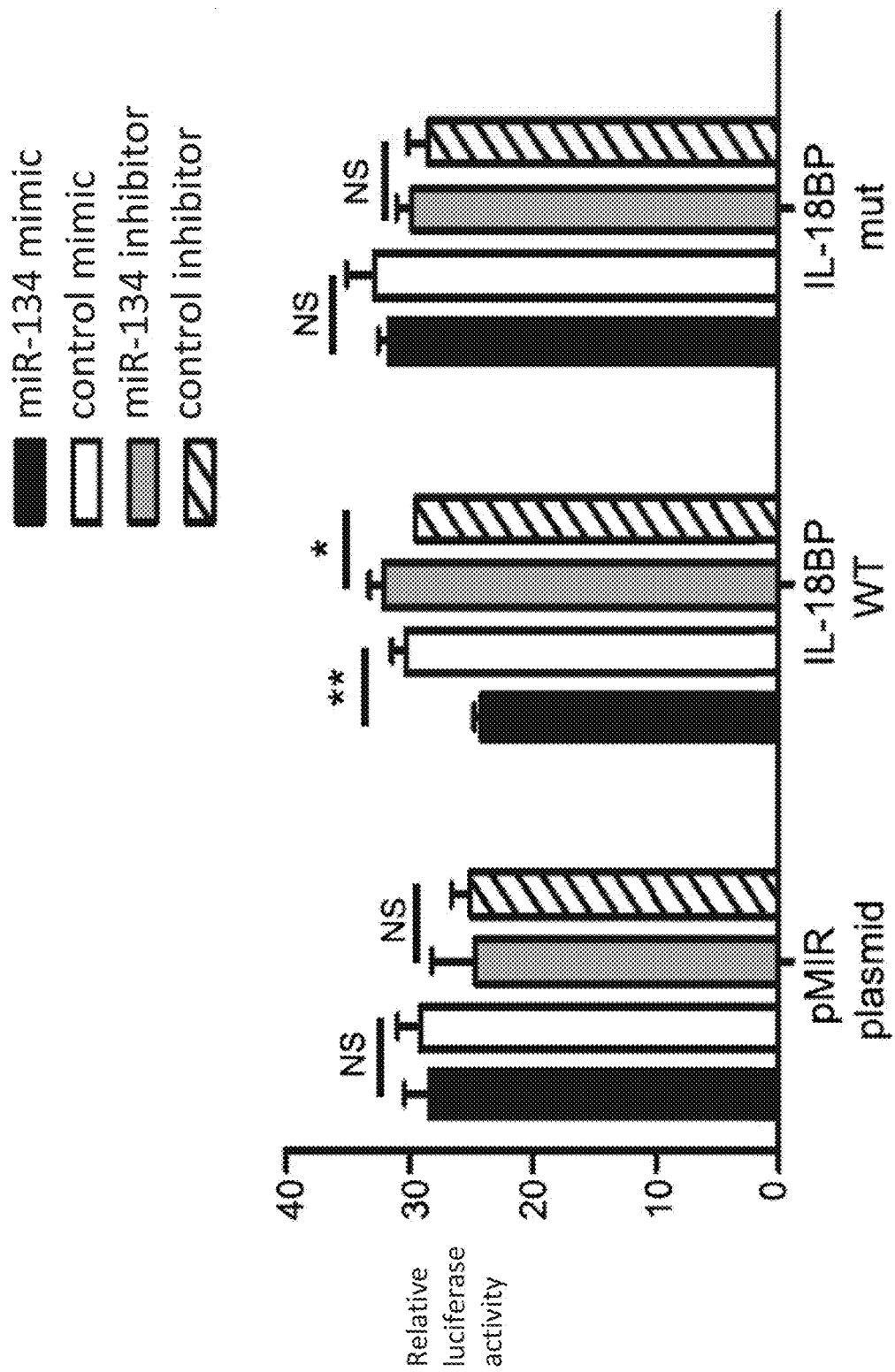
FIG. 8 shows the luciferase activities detected in 293T cells received various transfection treatments.

After each group of cells was incubated for 36 hrs, the luciferase activity was analyzed with the Dual-Glo luciferase detection system (Promega). The results are shown in FIG. 8. From the results in FIG. 8, it can be seen that compared with the cells transfected with the mutant human IL-18BP 3'UTR luciferase reporter plasmid, when the cells are transfected with wild human IL-18BP 3' UTR-luciferase reporter plasmid, the miR-134 mimic reduces the luciferase activity, and the miR-134 inhibitor increase the luciferase activity. This suggests that IL-18BP is a target of miR-134 and is down-regulated by miR-134.

Figure 9A:
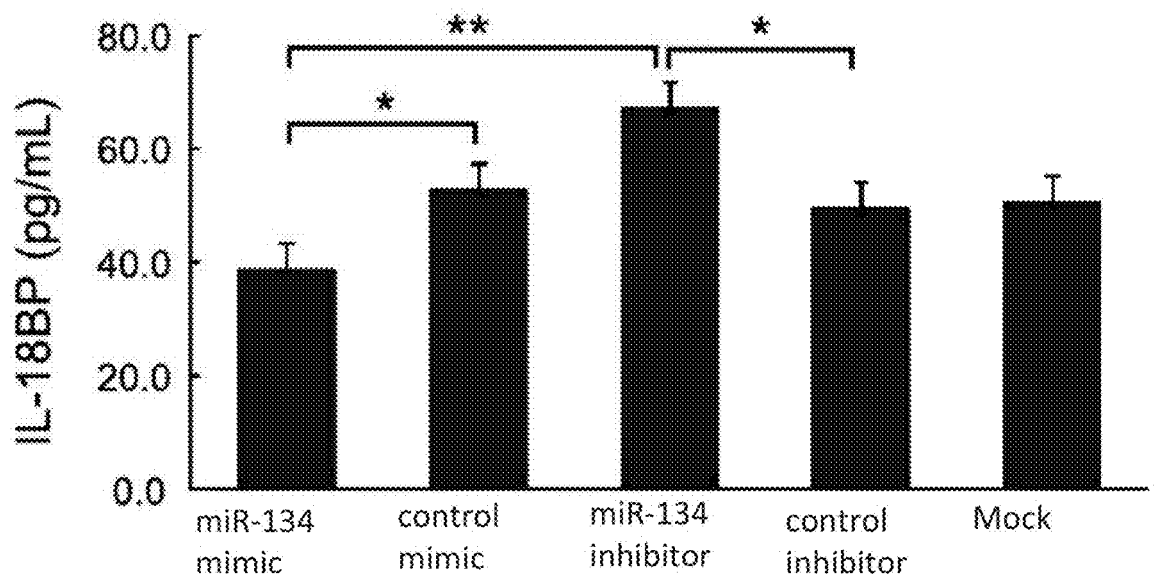
FIG. 9A shows the IL-18BP expressions detected in THP-1 cells received various transfection treatments.
Figure 9B:
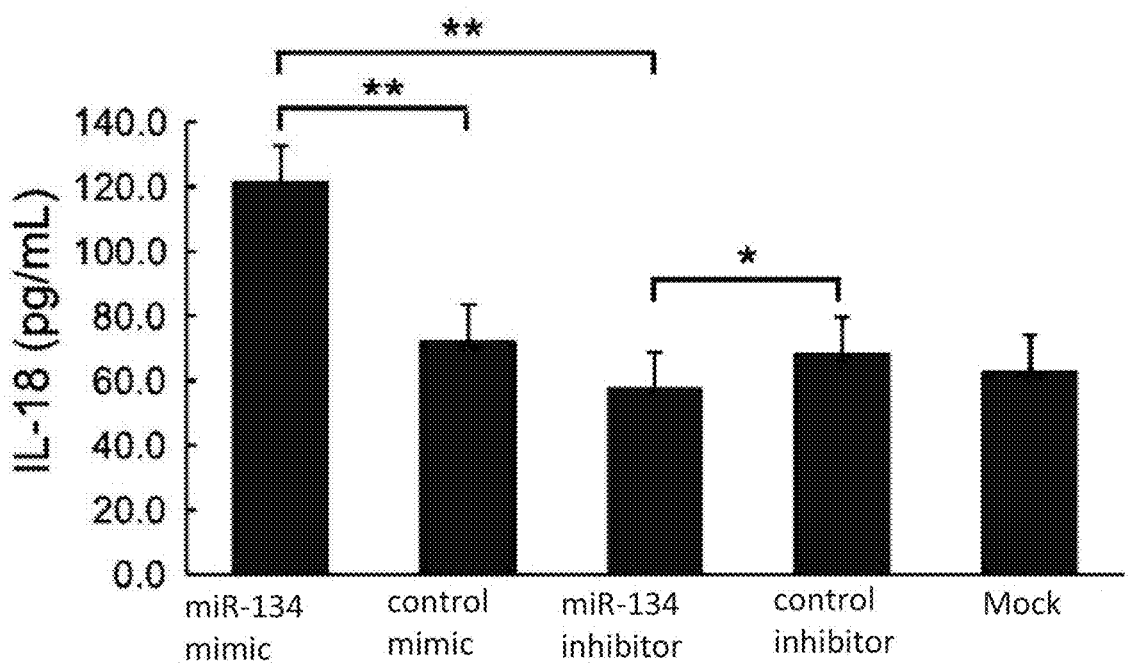
FIG. 9B shows the IL-18 expressions detected in THP-1 cells received various transfection treatments.

Moreover, the expression levels of IL-18BP and IL-18 in each group of THP-1 cells transfected with the miR-134 mimic, the control mimic, the miR-134 inhibitor, or the control inhibitor, and in the cells of the untransfected mock group were detected by using an ELISA kit (R&D Systems, USA). The results are shown in FIG. 9. As can be known from the results shown in FIG. 9A and FIG. 9B, miR-134 is over expressed in the group of cells transfected with the miR-134 mimic, in which the average expression level of IL-18BP is 38.6 pg/ml, and the average expression level of IL-18 is 121.3 pg/ml. Compared with the miR-134 mimic group, the average expression level of IL-18BP in the miR-134 inhibitor group, the control mimic group, and the mock group is 67.2 pg/ml, 52.7 pg/ml, and 50.4 pg/ml respectively, and the average expression level of IL-18 is 57.3 pg/ml, 72.0 pg/ml, and 62.5 pg/ml respectively.

The above results show that the over-expression of miR-134 obviously reduces the intracellular expression of IL-18BP, causing the increase of IL-18.

Example 12: Correlation Between miR-134 and IL-18BP and IL-18

Following the process as described in Example 8, the intracellular expressions of miR-134 and IL-18BP mRNA in the TLR3 ligand-stimulated peripheral blood mononuclear cells derived from patients with AOSD and healthy subjects were detected. The correlation between the IL-18BP and IL-18 expressions and the miR-134 expression was analyzed. The results are shown in FIG. 10.

Figure 10A:
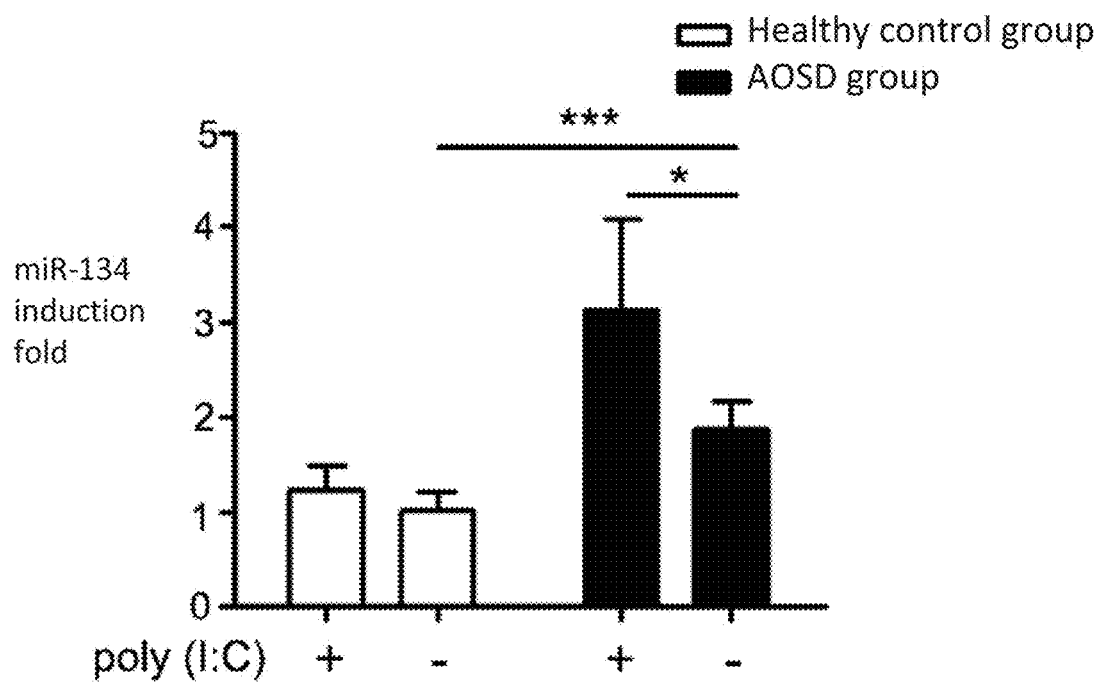
FIG. 10A shows the intracellular miR-134 expressions detected in TLR3 ligand-stimulated peripheral blood mononuclear cells derived from subjects in a healthy control group and patients having AOSD.
Figure 10B:
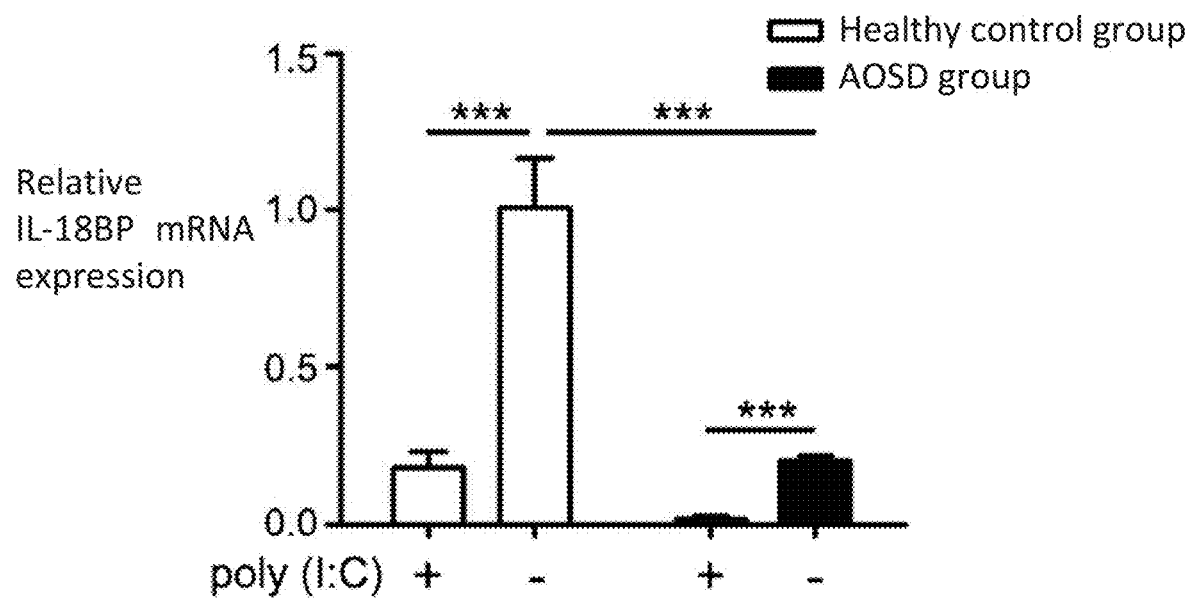
FIG. 10B shows the intracellular IL-18BP mRNA expressions detected in TLR3 ligand-stimulated peripheral blood mononuclear cells derived from subjects in a healthy control group and patients having AOSD.
Figure 10C:
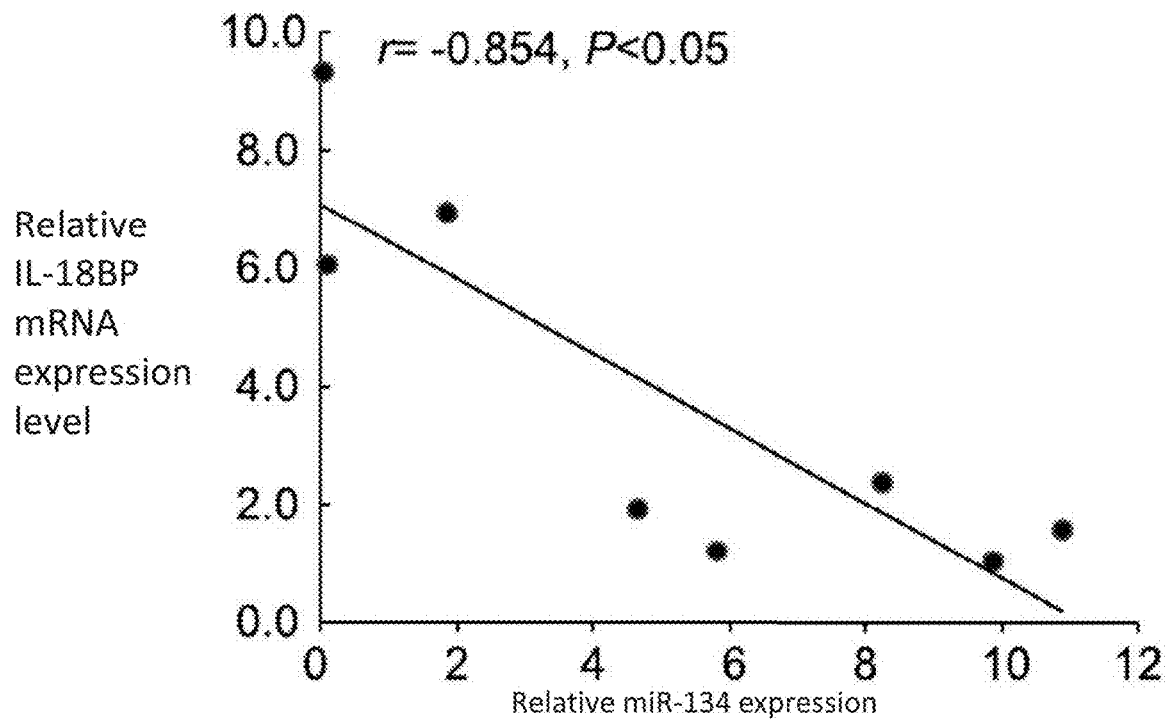
FIG. 10C shows the correlation between the miR-134 expression and the IL-18BP mRNA expression.
Figure 10D:
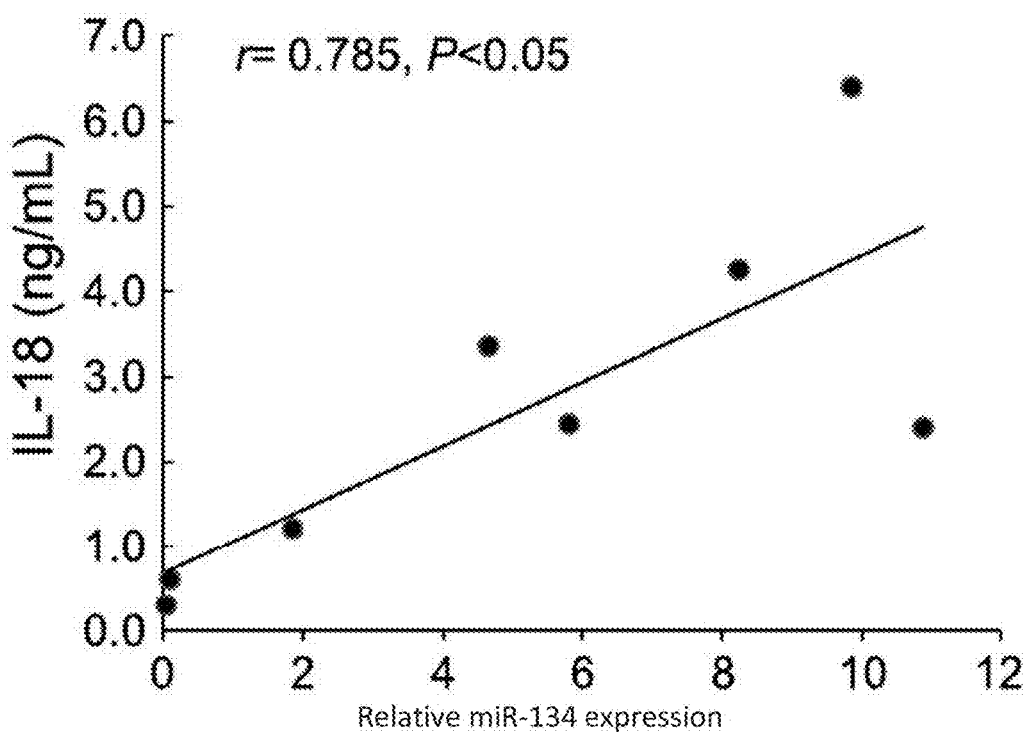
FIG. 10D shows the correlation between the miR-134 expression and the IL-18 expression.
Figure 10E:
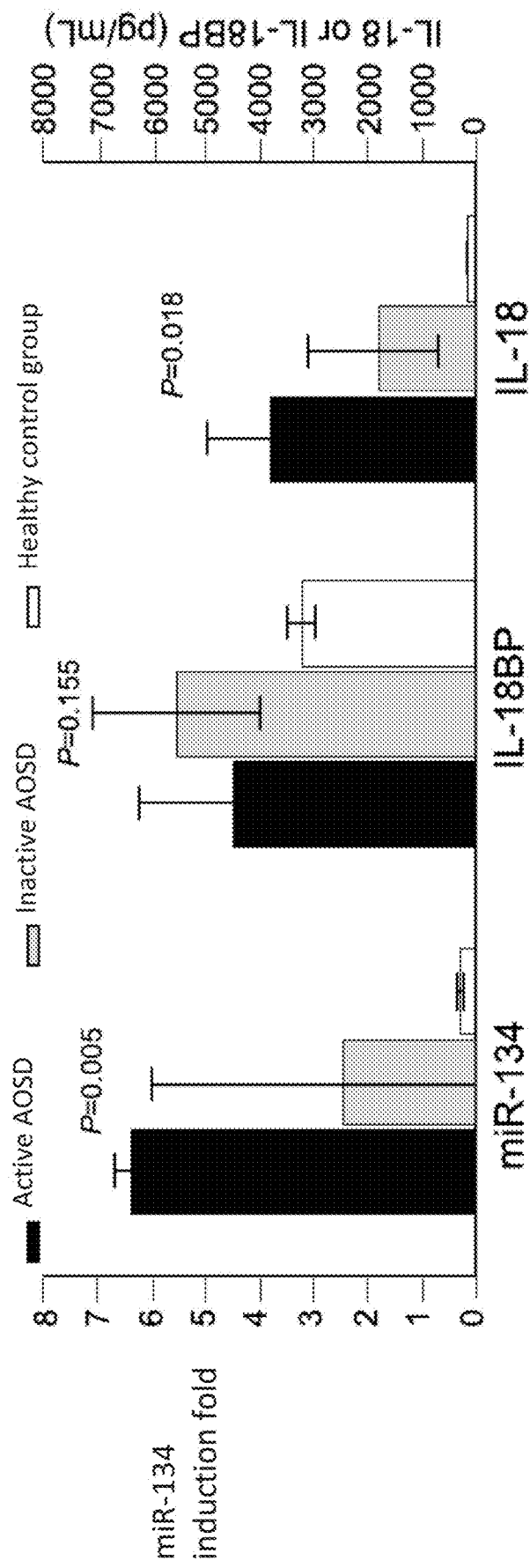
FIG. 10E shows the in-vivo miR-134, IL-18BP, and IL-18 expressions in patients with active AOSD, patients with inactive AOSD, and subjects in healthy control group.

It can be known from FIG. 10A and FIG. 10B that after in-vivo stimulation with a TLR3 ligand in the patients with AOSD, the expression level of miR-134 is increased, and the expression level of IL-18BP mRNA is reduced. Further, as can be seen from the results shown in FIG. 10C and FIG. 10D, the miR-134 expression is negatively correlated with the IL-18BP mRNA expression, and the miR-134 expression is positively correlated with the plasma IL-18 expression in the patients with AOSD. FIG. 10E further shows that in patients with active AOSD, the IL-18BP expression level is 5572.5 pg/ml, the IL-18 expression level is 3844.0 pg/ml, and the miR-134 expression level is 6.4 folds; in patient with inactive AOSD, the IL-18BP expression level is 4441.6 pg/ml, the IL-18 expression level is 1863.6 pg/ml, and the miR-134 expression level is 2.4 folds; and in subjects of the healthy control group, the IL-18 expression level is 112 pg/ml and the miR-134 expression level is 0.3 folds.

What is claimed is:

1. A method for treating adult-onset Still's disease (AOSD) and detecting the therapeutic effectiveness for adult-onset Still's disease (AOSD), which comprises:
   detecting the therapeutic effectiveness for adult-onset Still's disease (AOSD), comprising:
   detecting the expression of a biomarker to obtain a first expression level, wherein the biomarker is selected from the group consisting of miR-134 and miR-223;

administering a treatment selected from the group consisting of methotrexate, hydroxychloroquine, sulfasalazine and tocilizumab;

after the treatment is received, detecting the expression of the biomarker, to obtain a second expression level; and comparing the first expression level with the second expression level, where when the second expression level is higher than the first expression level, the treatment is shown to be ineffective in the treatment of AOSD; and when the second expression level is lower than the first expression level, the treatment is shown to be effective in the treatment of AOSD.

2. The method for treating AOSD and detecting the therapeutic effectiveness for adult-onset Still's disease (AOSD) according to claim 1, wherein the treatment is capable of reducing the expression of miR-134 and miR-223 in the individual.

3. The method for treating AOSD and detecting the therapeutic effectiveness for adult-onset Still's disease (AOSD), according to claim 1, wherein the technique for detecting the biomarker is ELISA or PCR.

* * * * *

SEQUENCE LISTING

```
<160> NUMBER OF SEQ ID NOS: 3

<210> SEQ ID NO 1
<211> LENGTH: 23
<212> TYPE: DNA
<213> ORGANISM: human

<400> SEQUENCE: 1
ugccugaaag agacacaguc aca                                             23

<210> SEQ ID NO 2
<211> LENGTH: 22
<212> TYPE: RNA
<213> ORGANISM: human

<400> SEQUENCE: 2
ggggagacca guuggucagu gu                                              22

<210> SEQ ID NO 3
<211> LENGTH: 23
<212> TYPE: DNA
<213> ORGANISM: human

<400> SEQUENCE: 3
ugccugaaag agacacugac uca                                             23
```